US012616811B2

(12) United States Patent
Hepting et al.

(10) Patent No.: US 12,616,811 B2
(45) Date of Patent: May 5, 2026

(54) EMERGENCY VENTILATOR WITH A FAN WHICH IS COOLED IN A CONDUCTIVE AND CONVECTIVE MANNER

(71) Applicant: Hamilton Medical AG, Bonaduz (CH)

(72) Inventors: Daniel Hepting, Maladers (CH); Jan Hunger, Chur (CH)

(73) Assignee: Hamilton Medical AG, Bonaduz (CH)

( * ) Notice: Subject to any disclaimer, the term of this patent is extended or adjusted under 35 U.S.C. 154(b) by 687 days.

(21) Appl. No.: 18/013,693

(22) PCT Filed: Jul. 6, 2021

(86) PCT No.: PCT/EP2021/068636
§ 371 (c)(1),
(2) Date: Dec. 29, 2022

(87) PCT Pub. No.: WO2022/013006
PCT Pub. Date: Jan. 20, 2022

(65) Prior Publication Data
US 2023/0330371 A1     Oct. 19, 2023

(30) Foreign Application Priority Data

Jul. 13, 2020    (DE) ..................... 10 2020 118 466.2

(51) Int. Cl.
| | |
|---|---|
| *A61M 16/00* | (2006.01) |
| *F04D 29/42* | (2006.01) |
| *F04D 29/58* | (2006.01) |

(52) U.S. Cl.
CPC ..... *A61M 16/0066* (2013.01); *F04D 29/4226* (2013.01); *F04D 29/5806* (2013.01);
(Continued)

(58) Field of Classification Search
CPC .......... A61M 16/0057; A61M 16/0063; A61M 16/0066; A61M 16/125;
(Continued)

(56) References Cited

U.S. PATENT DOCUMENTS

| | | |
|---|---|---|
| 4,794,922 A | 1/1989 | DeVries |
| 9,861,774 B2 | 1/2018 | Fu et al. |

(Continued)

FOREIGN PATENT DOCUMENTS

| | | | |
|---|---|---|---|
| EP | 3391924 A1 | 10/2018 | |
| WO | WO-2008098382 A1 * | 8/2008 | ............. H02K 9/227 |

OTHER PUBLICATIONS

International Preliminary Report on Patentability for corresponding PCT/EP2021/068636 mailed Jan. 17, 2023, 6 pgs.
(Continued)

*Primary Examiner* — Joseph D. Boecker
(74) *Attorney, Agent, or Firm* — Rankin, Hill & Clark LLP

(57) ABSTRACT

An emergency ventilator for artificially ventilating patients in the event of a medical emergency, having: —a housing with an ambient air suction opening and a ventilating gas outlet opening and—a fan which is designed and is arranged in the housing so as to convey ambient air from the ambient air suction opening to the ventilating gas outlet opening, wherein the fan includes a fan housing with an air conveyor which can be moved relative to the fan housing, and the fan housing is arranged in the housing in a fixed manner thereto; the fan housing is secured to the housing with the interposition of a heat conducting body, the heat conducting body including or being made of a material which is selected from light metal, nonferrous metal, and/or a plastic filled with a heat-conductive filler material.

21 Claims, 7 Drawing Sheets

(52) U.S. Cl.
CPC ... *A61M 16/0069* (2014.02); *A61M 2205/125*
(2013.01); *A61M 2205/3606* (2013.01); *A61M*
*2205/8206* (2013.01)

(58) Field of Classification Search
CPC ... A61M 2205/3606; A61M 2205/3666; F04D
29/4226; F04D 29/5806
See application file for complete search history.

(56) References Cited

U.S. PATENT DOCUMENTS

| | | | | |
|---|---|---|---|---|
| 2007/0048159 A1* | 3/2007 | DiMatteo | .......... | A61M 16/0066 |
| | | | | 417/423.14 |
| 2009/0136341 A1* | 5/2009 | Kenyon | .............. | F04D 25/0606 |
| | | | | 415/203 |
| 2012/0138058 A1* | 6/2012 | Fu | ....................... | F04D 25/0666 |
| | | | | 128/204.23 |
| 2013/0263854 A1* | 10/2013 | Taylor | ................. | A61M 16/203 |
| | | | | 128/204.23 |
| 2019/0226495 A1* | 7/2019 | Kanai | ...................... | H02K 5/18 |
| 2019/0366025 A1* | 12/2019 | Diehl | ............... | A61M 16/0003 |

OTHER PUBLICATIONS

German Search Report for corresponding DE 10 2020 118 466.2
mailed Mar. 1, 2021, 8 pgs.
International Search Report for corresponding PCT/EP2021/068636
mailed Oct. 28, 2021, 13 pgs.
Espacenet Bibliographic data: EP 3391924 (A1), Published Oct. 24,
2018, 1 pg.

* cited by examiner

EMERGENCY VENTILATOR WITH A FAN WHICH IS COOLED IN A CONDUCTIVE AND CONVECTIVE MANNER

This application claims priority in PCT application PCT/EP2021/068636 filed on Jul. 6, 2021, which claims priority in German Patent Application DE 10 2020 118 466.2 filed on Jul. 13, 2020, which are incorporated by reference herein.

The present invention concerns an emergency ventilator for emergency medicine artificial respiration of patients, comprising A housing with an ambient air aspiration aperture and a respiratory gas output aperture, and A fan which is configured and arranged in the housing in order to convey ambient air from the ambient air aspiration aperture to the respiratory gas output aperture, Where the fan comprises a fan housing with an air conveyor movable relative to the fan housing and where the fan housing is arranged housing-tight in the housing.

BACKGROUND OF THE INVENTION

As such an emergency ventilator there are known the mobile ventilator with the designation 'EOVE-150 Ventilator' of EOVE SA in Pau (FR), the mobile ventilator with the designation 'EVEN$_{IN}$' of Fritz Stephan GmbH in Gackenbach (DE), and the mobile ventilator with the designation 'Falco 202 Evo' of the Italian firm Siare Engineering International Group s. r. l. in Valsamoggia (IT).

From EP 3 391 924 A1 there is known a mobile ventilator whose respiratory gas flow is guided as a convective cooling gas flow along a wall of the ventilator with which a storage battery is in contact as an energy store of the ventilator. Thereby, heat of the storage battery should be dissipated away from the respiratory gas flow in order to cool the storage battery and thus make possible shorter charging times.

Emergency ventilators, inter alia also referred to as 'intensive care ventilators', serve for rapid supply of respiratory gas to a patient outside a clinical environment, i.e. for instance at an accident site and/or during transportation of a patient. Of course, emergency ventilators can also be used in a clinical environment, however in hospitals often more powerful ventilators are available as emergency ventilators.

The fan with the fan housing which is static relative to the housing of the emergency ventilator and the air conveyor which is accommodated movably in the fan housing and is moving during a ventilation operation produces, like all devices with components which are mounted on each other and are relatively movable, heat due to friction and due to electric resistance in an electric drive of the air conveyor. An other than electric drive is indeed possible in principle, but on practical grounds is out of the question.

From WO 2008/098382 A1 of the present applicant there is known a fan for a ventilator which for mitigating the sound emission is cooled by a heat pipe, less frequently also referred to as 'Wärmerohr' in German.

SUMMARY OF THE INVENTION

It is the task of the present invention to protect the fan as heat source of the emergency ventilator against overheating and to this end as far as possible not increase the weight of the emergency ventilator, such that it remains usable as a portable ventilator without further restriction.

The present invention solves this task through an emergency ventilator, as mentioned in the beginning, in which additionally the fan housing is fixed to the housing with the interposition of a heat-conducting body, where the heat-conducting body comprises a material or is made from a material which is chosen out of light metal, non-ferrous metal, and/or a synthetic filled with heat-conducting filling material. Consequently the fan housing can give off heat arising in the fan to the heat-conducting body at least through heat conduction but possibly also through additional physical principles of heat transport such as radiation and convection. The emergency ventilator can transfer the heat transferred from the fan housing to the heat-conducting body via its housing to the external environment of the emergency ventilator.

Since in any case the fan has to be arranged housing-tight in the housing of the emergency ventilator, through suitable choice of material of the structure fastening the fan housing heat arising in the fan can be given off to the housing and from there to the environment. An additional cooling structure is consequently not necessary. The structure fastening the fan housing is made in order to ensure its sufficient heat conductance at least in part, preferably completely, from at least one of the mentioned materials. Due to the focus of the structure not only on the fixing of the fan in the housing but also on the dissipation of heat from the fan during the fan's operation and thereafter, the structure of the present application which fastens the fan housing is denoted as 'heat-conducting body'.

'Housing-tight' here does not necessarily mean configured directly at the housing, although this is also comprised by the term 'housing-tight'. 'Housing-tight' means 'in normal use, not separable and/or not removable respectively from the housing except for any repair purposes'.

Out of the materials mentioned, light metal is preferable since it exhibits not only very high strength but likewise high heat conductance with relatively low density. In most synthetics filled with heat-conducting material, the density is indeed even lower than in light metals, but the heat conductance is also less. Non-ferrous metals usually likewise exhibit outstanding heat conductance, but in most cases along with higher density than light metals and filled synthetics.

The fan exhibits of course a drive which sets the air conveyor in motion relative to the fan housing in order to convey respiratory gas in the direction towards the respiratory gas output aperture. Since in the emergency ventilator discussed here, the respiratory gas supplied to the patient normally contains ambient air, where into the latter there can be mixed at least one special gas different from ambient air, the respiratory gas-conveying formation of the fan which is movable relative to the fan housing is designated as 'air conveyor'. In most cases, the air conveyor is a rotationally movable air conveyor, for example an impeller wheel or turbine wheel. A constant airflow can thus be produced during the operation of the fan.

The special gas, normally oxygen or an anesthetic, such as for instance laughing gas, can be introduced into the housing through a special gas coupling section and/or through a special gas auxiliary inlet. The emergency ventilator preferably exhibits a mixing chamber, in which different gases introduced and/or aspirated into the housing are mixed as the respiratory gas. The special gas coupling section is configured for detachable coupling with an oxygen supply or an oxygen reservoir when in normal use, for instance in the form of a quick coupling.

The drive of the fan can be arranged outside or inside the fan housing. The drive is preferably arranged in the fan housing, in order to be able on the one hand to shield the drive through the fan housing from outside influences and in order to be able on the other hand also to transfer heat from the drive via the fan housing to the heat-conducting body.

As stated at the beginning, the air conveyor is accommodated in the fan housing.

The fan housing can be configured at least in two parts and comprise a drive housing part which accommodates the drive and a conveyor housing part which accommodates the air conveyor. For improved heat conduction, the drive housing part can be made from a first material, for instance metal, in particular from an aluminum alloy, whereas the conveyor housing part can be fabricated from a second material different from the first one. Since it can be sufficient for the conveyor housing part to shield the air conveyor mechanically against external influences, the conveyor housing part can be fabricated from a synthetic as the second material, for instance as a multipart injection-molded component. The conveyor housing part can be fixed at the drive housing part.

The emergency ventilator exhibits a control device which is configured to operate the fan only during inspiration phases, in which respiratory gas is supplied to a patient. During expiration phases, in contrast, the fan is not operated which not only reduces the heat development in the fan over the entire duration of an artificial respiration, but also extends the useful life of a charged electric energy store. The electric energy store, preferably a repeatedly rechargeable storage battery, is accommodated in an accommodating compartment in the housing of the ventilator. The accommodating compartment is preferably separated structurally from the heat-conducting body, for instance through an inner housing partition. Additionally or alternatively, the accommodating compartment is configured outside the fan housing, especially preferably also separated structurally from the latter. This structural separation can again be realized through the inner housing partition already mentioned. The inner housing partition is a partition in the housing of the ventilator, not in the fan housing.

In order to facilitate the assembly of the fan, the fan housing is preferably configured in several parts and exhibits for example at least two or even more housing components connected with one another.

In the known appliance 'EOVE-150 Ventilator' mentioned at the beginning, the fan housing is made of a synthetic and is mounted in a floating manner, i.e. with a certain freedom of movement, in the housing of the ventilator which is likewise made of a synthetic. Consequently, nearly exclusively convective cooling of the EOVE appliance is achieved. However, the freedom of movement of the EOVE appliance which is provided precisely in the region of the rotating air conveyor can have negative effects on the rotational mounting and the rotational operation of the known air conveyor.

Preferably, therefore, in the emergency ventilator of the present invention the fan housing is connected rigidly with the heat-conducting body. The fan housing can be configured with at least one fan housing component integral with the heat-conducting body, which makes possible especially high heat conduction efficiency since no thermal resistances in the form of air gaps and the like are present. Alternatively, the fan housing can be firmly bonded with the heat-conducting body, for instance through welding, soldering, or gluing. Further alternatively, the fan housing can be connectable or connected with the heat-conducting body with heat-conducting fasteners such as metal bolts or mutually pluggable, complementary projections and recesses in the fan housing on the one hand and in the heat-conducting body on the other.

Between the fan housing and a fan joint-face of the heat-conducting body which faces towards the fan housing there can be arranged heat-conductive paste or a heat-conductive mat in order to physically bridge any air gaps. The heat-conductive mat is here preferable to the heat-conductive paste, since heat-conductive paste could reach the respiratory gas flow through difficult to control flow. The heat-conductive mat as a solid body, in contrast, cannot flow.

Since normally the drive of the fan constitutes the most powerful heat source of the fan during the operation of the fan, preferably a section of the fan housing which surrounds the drive of the fan, for instance the aforementioned drive housing part, is arranged to lie opposite the fan joint-face, where applicable with the interposition of heat-conductive paste or a heat-conductive mat. In order to minimize the thermal resistance, preferably an outer surface of the section of the fan housing which surrounds the drive of the fan abuts against the fan joint-face.

Likewise, in order to ensure the most stable bond possible, the heat-conducting body can be connected rigidly with the housing. This achieves not only mechanical stability and robustness, but also ensures permanently heat conductance from the fan to an outer wall of the housing of the emergency ventilator. Again, the heat-conducting body can be configured integrally with a section of the housing of the emergency ventilator, which indeed for a given structural shapes makes for the best possible, because lowest-resistance heat conduction, but restricts freedom of design in the designing of the heat-conducting body and possibly also of the fan housing. Preferably, therefore, the heat-conducting body is configured separately from the housing and connected with the latter through fasteners, for example through bolts, with which a housing joint-face with which the heat-conducting body faces towards the housing, can be clamped against a wall surface of the housing. Through this clamping option, in turn, any gap present as a thermal resistance between the heat-conducting body and the housing can be minimized.

Between the heat-conducting body, in particular the housing joint-face, and the housing there can also be arranged heat-conductive paste or a heat-conductive mat for decreasing a thermal resistance. For the aforementioned reasons, the use of a heat-conductive mat is preferable. Preferably, in order to achieve the smallest possible thermal resistances, any gap dimension between the fan joint-face and the fan housing and between the housing joint-face and the housing is each smaller than 1 mm, more preferably smaller than 0.3 mm.

In some ventilators, from the respiratory gas conveyed by the fan there branches off a part-flow as a cooling gas flow and fed to components which require cooling. This is unnecessary in the emergency ventilator discussed here. The respiratory gas flow conveyed by the fan can be supplied completely to the patient without a part-flow branching off from it.

Nevertheless, in the emergency ventilator of the present invention too, the respiratory gas conveyed by the fan can transport heat convectively away from the fan and/or from the heat-conducting body. Warming of the respiratory gas effected thereby is even desirable, since it prevents or at least reduces condensation dissolved in respiratory gas during transport to the patient.

In order to achieve convective cooling through the respiratory gas flow, the heat-conducting body can exhibit at least one duct routed in the heat-conducting body, which forms at least part of a flow path from the ambient air aspiration aperture to the respiratory gas output aperture in such a way that during the ventilation operation of the emergency ventilator, flow through the duct of respiratory gas conveyed by the fan to the respiratory gas output aperture is possible. The part of the respiratory gas flowing through the duct too, where preferably the entire respiratory gas flows through the duct, is supplied to the patient as respiratory gas. The duct can comprise several part-ducts.

When the heat-conducting body is fabricated in an especially economical way through extrusion pressing or extrusion molding, the at least one duct can already be formed during extrusion pressing or during extrusion molding. Such a duct, however, does not have to be formed.

Additionally or alternatively, the respiratory gas flow conveyed by the fan can directly carry heat away from the fan. In order to achieve this to the greatest possible extent, it is advantageous if an outer surface of the fan housing is exposed in a section of a flow path from the ambient air aspiration aperture to the respiratory gas output aperture in such a way that during the ventilation operation of the emergency ventilator it can be wetted by respiratory gas conveyed by the fan. The area segment of the outer surface of the fan housing which can be bathed by the respiratory gas then serves directly for convective release of heat to the respiratory gas which flows against the bathed area segment.

Since in any case the respiratory gas flows through a section of the fan housing, namely the section of the fan housing which accommodates a conveying formation of the air conveyor, a section of the fan housing which houses the air conveyor exhibits an area segment large relative to the rest of the fan housing which can effectively transfer heat to gas flowing past it and in this process bathes it. Preferably, therefore, the part of the fan housing which can be bathed by respiratory gas, can be bathed by respiratory gas on two opposite sides, namely on its inside and on its outside. Therefore, as already set out above, preferably a part of the fan housing which surrounds the drive, for instance the aforementioned drive housing part, is connected with the heat-conducting body and optionally recessed in a recess of the heat-conducting body. Furthermore, a part of the fan housing which movable the air conveyor is situated in a volume region filled with respiratory gas, for instance in a mixing chamber and/or in a flow chamber for having respiratory gas flowing through it, when the latter is conveyed from the ambient air aspiration aperture and/or from the special gas coupling section and/or from the special gas auxiliary inlet to the respiratory gas output aperture.

When the air conveyor, as is preferable, is an air conveyor rotationally movable relative to the fan housing, at least one surface region of the outer side of the fan housing which can be bathed by respiratory gas is a surface region surrounding a rotational axis of the air conveyor, preferably surrounding completely along a closed path. Thus eddies arising in the external environment of the fan housing through the movement of the air conveyor can be utilized for increasing the convectively dissipated heat quantity.

At least one section of the fan housing thus forms a wall of a region enclosing a respiratory gas, i.e. for instance a wall of the mixing chamber and/or of the flow chamber of the respiratory gas. At this point let it be noted that the mixing chamber is also part of a flow chamber of the respiratory gas, since the respiratory gas located in the mixing chamber is also conveyed to the respiratory gas output aperture.

A section of the surface of the heat-conducting body also preferably forms a wall of a region enclosing a respiratory gas, i.e. for instance a wall of the mixing chamber and/or of the flow chamber of the respiratory gas. Thus the heat-conducting body, into which heat is introduced from the fan, in particular from the fan drive, is cooled not only through the housing towards the environment but also through forced convection by means of the conveyed respiratory gas.

The heat-conducting body can not only ensure heat dissipation from the housing, but as a structural component can additionally impart stability to the emergency ventilation chamber. To this end, the heat-conducting body can surround a section of the flow path of the respiratory gas, for instance the aforementioned mixing chamber, on at least three sides, preferably on four sides, forming a recess. In this recess there can then be arranged the part of the outer surface of the fan housing which can be bathed by respiratory gas, in order to make sure that the part of the outer surface which can be bathed is also actually bathed by respiratory gas during the greatest possible proportion of the time of the emergency ventilator's operation.

In order to be able to ensure that the fan housing also has sufficiently good heat-conducting properties in order to conduct heat from the inside of the fan housing to the outside and/or from a region which surrounds the fan drive into a region which surrounds the air conveyor, it is preferable for the fan housing to comprise a material or be made from a material which is chosen out of light metal, non-ferrous metal, and/or a synthetic filled with heat-conducting filling material.

Preferably the fan housing can be made at least sectionwise, preferably completely, from the same material as the heat-conducting body.

Likewise, it is advantageous for sufficient heat conduction of the housing of the emergency ventilator if the housing comprises a material or is made from a material which is chosen out of light metal, non-ferrous metal, and/or a synthetic filled with heat-conducting filling material. To facilitate fabrication and assembly, the housing can be made from the same material as the heat-conducting body.

The light metal can comprise aluminum, magnesium, an aluminum alloy, and/or a magnesium alloy. These light metals exhibit good heat conductance with relatively low density and sufficiently high strength along with a low corrosion tendency.

The non-ferrous metal can comprise copper and/or a copper alloy. Known and suitable copper alloys are for example bronze and brass, where the exact composition of each can vary across a wide range. Copper and copper alloys exhibit exceptionally high heat conductance, but also have higher density and a higher corrosion tendency than light metals.

The heat-conducting filling material can comprise a metal, for example a light metal in the above sense, and/or a ceramic, and/or graphite, and/or carbon, in particular carbon nanotubes. Boron nitride is one known ceramic which with relatively low density, increases the heat conductance of a synthetic matrix in which the ceramic is embedded. In principle, any material which exhibits a heat conductance of at least 14 W/(mK) can serve as a suitable heat-conducting filling material.

The filling material can for example be accommodated in particle or fiber form in a synthetic matrix. The synthetic can be a thermoset or thermoplastic. In order to facilitate shaping, the synthetic is preferably a thermoplastic.

The fan joint-face of the heat-conducting body, which lies opposite a section of the fan housing, was already mentioned above, and likewise the housing joint-face of the heat-conducting body which faces towards an inner surface of the housing. For effective heat removal out of the emergency ventilator, it is advantageous if heat transported by the heat-conducting body can be transferred to the housing of the emergency ventilator across the largest possible area. Therefore the housing joint-face is at least twice as large, preferably at least four times as large, especially preferably at least six times as large as the fan joint-face.

The housing of the present emergency ventilator preferably has a simple housing shape, preferably with a prismatic and/or cylindrical basic form. Consequently the housing preferably has two end faces which are essentially parallel to one another and a lateral surface connecting the two end faces with one another. The lateral surface goes around a virtual prism axis which connects the end faces with one another. The lateral surface can be designed as polyhedral with planar surfaces which follow one another in the circumferential direction about the prism axis. To prevent injuries, the connecting regions between two planar lateral surface sections which are directly adjacent in the circumferential direction are rounded. The radius of curvature of such a connecting section is preferably at least 0.5 cm. The radius of curvature is preferably parallel to the prism axis. The lateral surface can equally be configured cylindrically, where the cross-sectional area of the cylindrical basic form can be circular or elliptical.

To achieve the largest possible housing joint-face, the latter preferably abuts against wall section of the housing which forms the lateral surface, where applicable with the superposition of the aforementioned heat-conductive paste or heat-conductive mat.

According to a further advantageous embodiment of the present invention, the heat-conducting body can be configured in several parts. For example, the heat-conducting body can exhibit on the fan housing side a body component and on the housing side a body component which is configured separately from the body component on the fan housing side. The body component on the fan housing side can exhibit the aforementioned fan joint-face and can be connected with the fan housing in a heat transferring manner in one of the ways described above. The body component on the housing side can exhibit the aforementioned housing joint-face and be connected with the housing of the ventilator in a heat transferring manner in one of the ways described above.

In an integral configuration of the heat-conducting body, the fan joint-face and the housing joint-face are configured in different regions of one and the same integral heat-conducting body and heat is transferred between these regions predominantly conductively through the material of the heat-conducting body.

In the multipart configuration, the mentioned body components can be connected with one another in a heat-transferring manner through at least one heat pipe, preferably through several heat pipes. For the sake of clarification we point out that instead of the common term 'heat pipe', sometimes the term 'Wärmerohr' is also used in the literature. In a heat pipe in general, a fluid in a normally elongated closed vessel, the pipe, is evaporated in a heat-absorption zone and condensed in a heat-emission zone. An internal structure of the heat pipe, often utilizing a capillary effect, ensures transport of the fluid in different states of matter between the heat-emission zone and the heat-absorption zone.

In the present case, preferably the heat-absorption zone of the at least one heat pipe is arranged in the body component on the fan housing side and its heat-emission zone in the body component on the housing side. In a region between the two mentioned body components, the at least one heat pipe can be exposed or penetrate through another body in whole or in part.

The at least one heat pipe is preferably curved at least regionally, in order to be able to utilize the installation space in the housing, i.e. in the housing of the ventilator, as affectively as possible for accommodating the heat pipe. For especially simple assembly, the at least one heat pipe exhibits an essentially straight heat-absorption zone and likewise an essentially straight heat-emission zone and exhibits a curved zone located between the mentioned zones. For the ventilator described here, it has turned out to be advantageous if the longitudinal axes of the heat-absorption zone and of the heat-emission zone of the at least one heat pipe exhibit an angle of between 70 and 110°, preferably between 80 and 100°, especially preferably of 90°. For the preferred case that several heat pipes are arranged for heat-transferring connection of the two body components of the heat-conducting body, preferably similar heat pipes are arranged in parallel side by side.

For the most effective heat transfer possible from the body component on the fan housing side to the heat-absorption zone of the heat pipe and from the heat-emission zone of the heat pipe to the body component on the housing side, the respective connections of body component and zone of the heat pipe are preferably formed through soldered connections. Thus air gaps as thermal resistances can be avoided.

The lateral surface can also be both prismatic and cylindrical, if for instance it is configured along a first circumferential section as polyhedral and along a second circumferential section adjoining the former as cylindrical or part-cylindrical, as the case may be. To facilitate the assembly of the heat-conducting body, the housing joint-face is preferably planar.

The fan for conveying respiratory gas is preferably the only fan or the only gas conveyor respectively in the emergency ventilator, such that separate cooling fans can be dispensed with.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
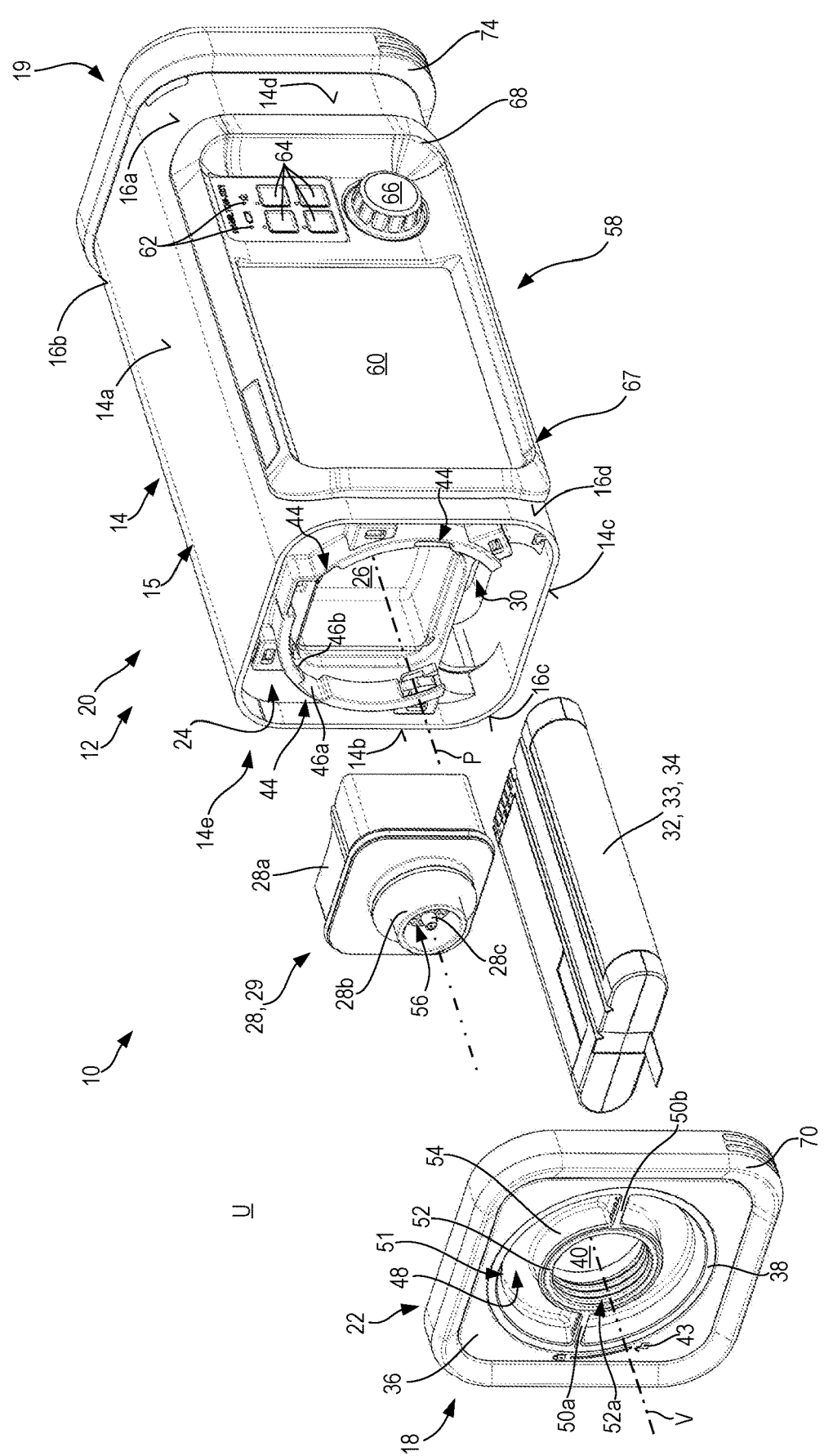
FIG. 1A perspective exploded view of a first embodiment of an emergency ventilator according to the invention, FIG. 2A longitudinal section through the first embodiment of the emergency ventilator according to the invention of FIG. 1, with a sectional plane parallel to the surfaces 14*b* and 14*d* in FIG. 1, FIG. 3A plan view of the one end face formed by a removable housing lid of the emergency ventilator of FIGS. 1 and 2, FIG. 4A plan view of the other, opposite end face of the emergency ventilator of FIGS. 1 and 2, FIG. 5A longitudinal section view along the sectional plane V-V of FIG. 7, FIG. 6A cross-section view along the sectional plane VI-VI of FIG. 7 which is orthogonal to the prism axis P, FIG. 7A plan view of the planar front face 14*d* with the input/output device 58 of the emergency ventilator of FIG. 1, and FIG. 8A cross-section view corresponding to the perspective of FIG. 6 of a second embodiment of an emergency ventilator according to the invention, viewed in a sectional plane orthogonal to the prism axis P.

Referring now to the drawings wherein the showings are for the purpose of illustrating preferred and alternative embodiments of the invention only and not for the purpose of limiting the same, in FIG. 1, a first embodiment according to the invention of an emergency ventilator is labelled generally by 10. The emergency ventilator 10 comprises a housing 12 with a prismatic basic form, in the present case with a cuboidal basic form.

The lateral surface 14 of the housing 12 comprises four planar area segments 14*a*, 14*b*, 14*c*, and 14*d*, of which planar area segments 14*a*, 14*b*, 14*c*, and 14*d* respectively following one another in the circumferential direction about the prism axis P are oriented orthogonally to one another. All planar area segments 14*a*, 14*b*, 14*c*, and 14*d* are parallel to the prism axis P. The planar area segments 14*a*, 14*b*, 14*c*, and 14*d* are connected with one another preferably without joints through quarter-cylindrical area segments 16*a*, 16*b*, 16*c*, and 16*d*. The individual cylinder axes of the quarter-cylindrical and thereby curved area segments 16*a*, 16*b*, 16*c*, and 16*d* are parallel to the prism axis P. The housing component 15 exhibiting the lateral surface 14 is preferably an extruded aluminum tube.

On the end face 18 of the housing 12 facing towards the observer of FIG. 1 the housing 12 comprises a housing lid 22 which is removable from the rest of the housing along the prism axis P and which can be arranged at the rest of the housing 20. The housing lid 22 consequently serves for capping a housing aperture 24 formed at the longitudinal end 14*e* lying nearer to the observer of FIG. 1 of the lateral surface 14. The housing aperture 24 is bounded by the lateral surface 14 of the rest of the housing 20. Through the housing aperture 24 there is accessible a filter accommodating compartment 26 for an air filter cartridge 28 with an air filter 29 and there is accessible a storage battery accommodating compartment 30 for a rechargeable electric storage battery 32 as a power-grid independent energy store 34.

The housing lid 22 exhibits a lid component 36 and a latching component 38. The latching component 38 is mounted at the lid component 36 rotatably about the latching axis V. In the locking state, i.e. when the housing lid 22 is arranged at the rest of the housing 20 and closes the housing aperture 24, the latching axis V proceeds coaxially with the prism axis P.

The housing lid 22 exhibits furthermore an ambient air aspiration aperture 40, which penetrates through both the lid component 36 and the latching component 38. Through the ambient air aspiration aperture 40, ambient air can be aspirated by a fan 42 (see FIG. 2) from the environment U through the air filter 29 into the housing 12.

The latching component 38 is shown in FIG. 1 in its latching position, from which it is rotatable anti-clockwise for instance by a twelfth of a rotation about the latching axis V into a releasing position denoted by a symbol 43 in the shape of an open padlock. The latching component 38 exhibits projections, which in FIG. 1 are hidden by the lid component 36, protruding radially in the direction away from the latching axis V. These projections are part of a bayonet latch, through which the housing lid 22 which closes the housing aperture 24 can be latched in a positive-locking manner to a latching counter-formation 44 which is immovable relative to the rest of the housing 20. The latching counter-formation 44 exhibits for this purpose several recesses 46, each with an axial recess section 46*a* and with a recess section 46*b* in the circumferential direction about the latching axis V. The projections of the latching component 38 can, when it is in the releasing position, be guided along the axial recess section 46*a* parallel to the latching axis V and thereby parallel to the prism axis P to the recess section 46*b* and after reaching the recess section 46*b* be moved in the circumferential direction along the recess section 46*b*.

The latching component 38 exhibits a recessed handle 48 proceeding in the circumferential direction, which is interrupted by two gripping bars 50*a* and 50*b* which lie diametrically opposite one another relative to the ambient air aspiration aperture 40 located between them. By manually gripping the gripping bars 50*a* and 50*b*, the latching component 38 can be rotated between the releasing position and the latching position and also the released housing lid 22 can be lifted off along the prism axis P from the rest of the housing 20 or attached onto the latter. The gripping bars 50*a* and 50*b* and the recessed handle 48 form together an actuating formation 51 for actuating the latching component 38.

Through one-handed operation, therefore, the housing lid 22 is removable from the rest of the housing 20 and also attachable to the latter and also in the closed position latchable and releasable.

The ambient air aspiration aperture 40 is directly bordered radially outwards—relative to the latching axis V—by a mounting section 52 of the lid component 36. The mounting section 52 exhibits an attachment formation 52*a* in the form of an inner thread. At this attachment formation 52*a* there can be arranged for example an additional air filter which fulfils filtering functions which the air filter 29 of the air filter cartridge 28 does not perform. Alternatively or additionally, there can be arranged at the attachment formation 52*a* a measuring device which records metrologically the aspirated ambient air flowing through the ambient air aspiration aperture 40, for instance determines its chemical composition or determines whether and where applicable to what extent the aspirated ambient air does or does not contain a predetermined constituent.

The mounting section 52 is surrounded radially outward by a mounting counter-section 54 of the latching component 38. The mounting section 52 acts so to speak as an axis component, which mounts the latching component 38 by means of its mounting counter-section 54 rotatably about the latching axis V. The mounting counter-section 54 forms a radial inner limit of the recessed handle 48.

The air filter cartridge 28 exhibits on its side which during operation faces towards the housing lid 22 an ambient air inlet aperture 56 which is bordered by a collar 28*b* protruding out from the cartridge main body 28*a*. In the operational state of the emergency ventilator 10, a cartridge inlet axis K which is conceived as penetrating centrally through the collar 28*b* is coaxial to the latching axis V and to the virtual prism axis P which is conceived as penetrating centrally through the lateral surface 14. The ambient air inlet aperture 56 is protected by a protective grille 57 (see FIG. 3) against ingress of larger dirt particles such a stones, dust balls and the like. The protective grille 57 can be configured by injection molding integrally with a housing part of the air filter cartridge 28 which exhibits the ambient air inlet aperture.

Concentrically to the collar 28*b* there projects along the cartridge inlet axis K a special gas auxiliary inlet 28*c* in the shape of a protruding connection nozzle which tapers away from the cartridge main body 28*a*. A special gas supply, for example an oxygen auxiliary supply, can be connected to the special gas auxiliary inlet 28*c* rapidly and in an uncomplicated manner, for example by an elastic hose which is sufficiently small or large as the case may be in its diameter being pushed onto the special gas auxiliary inlet 28*c* and held there in a frictionally engaged manner. Through the shape of the special gas auxiliary inlet 28*c* which tapers away from the cartridge main body 28*a*, hoses in a predetermined diameter range can be connected with the special gas auxiliary inlet 28*c* sufficiently securely on short notice.

The energy store 34 exhibits in the depicted preferred embodiment example a single energy store body 33.

On the planar area segment 14*d* and starting off from it extending into the part-cylindrical neighboring area segments 16*d* and 16*a*, the emergency ventilator 10 exhibits an input/output device 58 which serves for the information exchange between the operator and the emergency ventilator 10 and which serves for the control of the emergency ventilator 10 by the operator. The input/output device 58 exhibits a screen 60 as an output device, which preferably is a touchscreen, which in a touch-sensitive manner allows the input of information. The input/output device 58 moreover exhibits display LEDs 62 as further output device and exhibits by way of example pushbuttons 64 and a rotary switch 66 as input means.

As protection from impact-like stresses, the input/output device 58 can be surrounded by a framing component 67, in an exemplifying configuration as a shock-absorbing elastomer ring 68, for instance made from synthetic rubber, natural rubber, and the like. The framing component 67 surrounding the input/output device 58 can, however, also be formed as a synthetic injection-molded component from a thermoplastic synthetic.

The appliance lid 22 too, is surrounded by a shock-absorbing elastomer ring 70 encircling completely in a circumferential direction about the prism axis P. In the locking state the elastomer ring 70 covers part of the lateral surface 14 just as it does of the end face 18, such that the elastomer ring 70 protects the emergency ventilator 10 in the region of the appliance lid 22 both against axial and against radial impact stresses.

Figure 2:
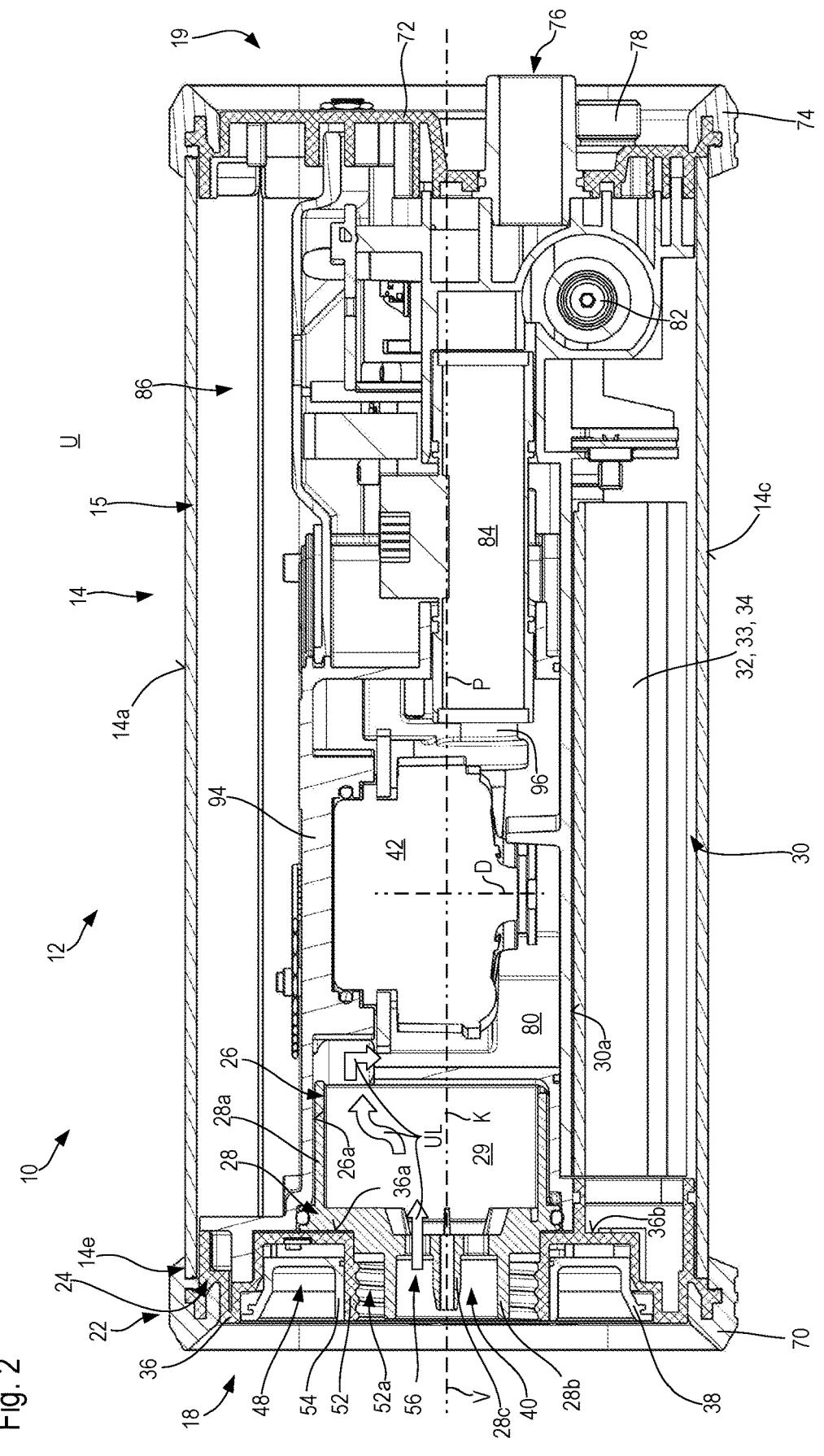

At the longitudinal end 14*f* of the lateral surface 14 opposite the appliance lid 22 there is likewise arranged an appliance lid 72 (see FIG. 2). In contrast to the appliance lid 22, however, the appliance lid 72 is preferably not removable from the lateral surface 14 of the housing 12. In order to also protect the longitudinal end of the appliance lid 72 from axial and radial impact stresses, at this longitudinal end too there is provided an elastomer ring 74 encircling the prism axis P completely in a closed manner in the circumferential direction, which covers both part of the lateral surface 14 and part of the end face 19. The end face 19 is opposite the end face 18.

To simplify fabrication, the elastomer rings 68, 70, and 74 are preferably made from the same soft elastic material.

FIG. 2 shows a longitudinal section through the emergency ventilator 10 along a sectional plane which contains the prism axis P and proceeds in parallel to the planar area segments 14*d* and 14*b*.

As is discernible in the operational locking state of the emergency ventilator 10 shown in FIG. 2, the lid component 36 exhibits a lid filter positioning section 36*a* which in the locking state is in abutting engagement with a section of the air filter cartridge 28, in particular with the cartridge main body 28*a*, thus contributing to a defined position of the air filter cartridge 28 and of the air filter 29 in the housing 12. The emergency ventilator further exhibits a housing filter positioning section 26*a*, for example in the shape of an inner wall of the filter accommodating compartment 26. Acting together, the lid filter positioning section 36*a* and the housing filter positioning section 26*a* define the operational position of the air filter cartridge 28 sufficiently accurately.

The lid component 36 likewise exhibits a lid-store positioning section 36*b* which in the depicted locking state is in abutting engagement with the energy store body 33, and acting together with a housing-store positioning section 30*a*, for instance an inner wall of the storage battery accommodating compartment 30, fixes the energy store body 33 sufficiently accurately in its operational position.

On the end face 19 in the housing-tight housing lid 72 there lies the respiratory gas output aperture 76 (see also FIG. 4), through which inspiratory respiratory gas conveyed by the fan 42 exits from the housing 12 towards a patient connected to the emergency ventilator 10.

Behind the sectional plane of FIG. 2, below the respiratory gas output aperture 76, there is provided, again in the housing-tight housing lid 72, a special gas coupling section 78, for instance a special gas connection nozzle, through which likewise a special gas different from ambient air can be introduced into the emergency ventilator 10. This special gas too, can for example be oxygen.

Consequently the emergency ventilator 10 permits the mixing of a respiratory gas from three different gases, namely from ambient air, from a first special gas introduced through the special gas coupling section 78, and from a second special gas introduced through the special gas auxiliary inlet 28*c*. If only one further special gas different from ambient air is needed for mixing the respiratory gas, it is preferably introduced via the special gas coupling section 78.

Ambient air UL aspirated through the ambient air aspiration aperture 40 enters, as depicted by the solid white arrows in FIG. 2, through the ambient air inlet aperture 56 into the cartridge main body 28*a*, passes through the air filter 29 and reaches a mixing chamber 80 in which the fan 42 with its aspiration aperture is arranged. The gas present in the mixing chamber 80 bathes a large part of the outer surface of the fan 42, thus contributing to its convective cooling.

A special gas introduced through the special gas coupling section 78, for example oxygen, can be suitably adjusted via the input/output device 58 in its mass flow through a variable proportional valve 82 and likewise via a special gas supply line 84 reaches the mixing chamber 80, where the ambient air UL and the special gas can already mix before entering the fan 42. Thus the fan 42 serves in the present case not only for conveying the respiratory gas but also for the most homogeneous mixing of the latter, such that the most homogeneous respiratory gas possible exits from the respiratory gas output aperture 76. The conveying line, which on the pressure side leads the respiratory gas from the fan 42 to the respiratory gas output aperture 76, lies in FIG. 2 behind the sectional plane of FIG. 2 and lies behind an electronics compartment 86 which is completely shielded physically against the special gas supply line 84 in order to exclude any ignition risk which a spark which could originate in the electronics accommodated in the electronics compartment 86 or even just sufficient heat in an environment of pure oxygen or highly elevated oxygen content could have. In the electronics compartment 86 there is accommodated a control device for controlling the operation of the emergency ventilator 10.

Figure 3:
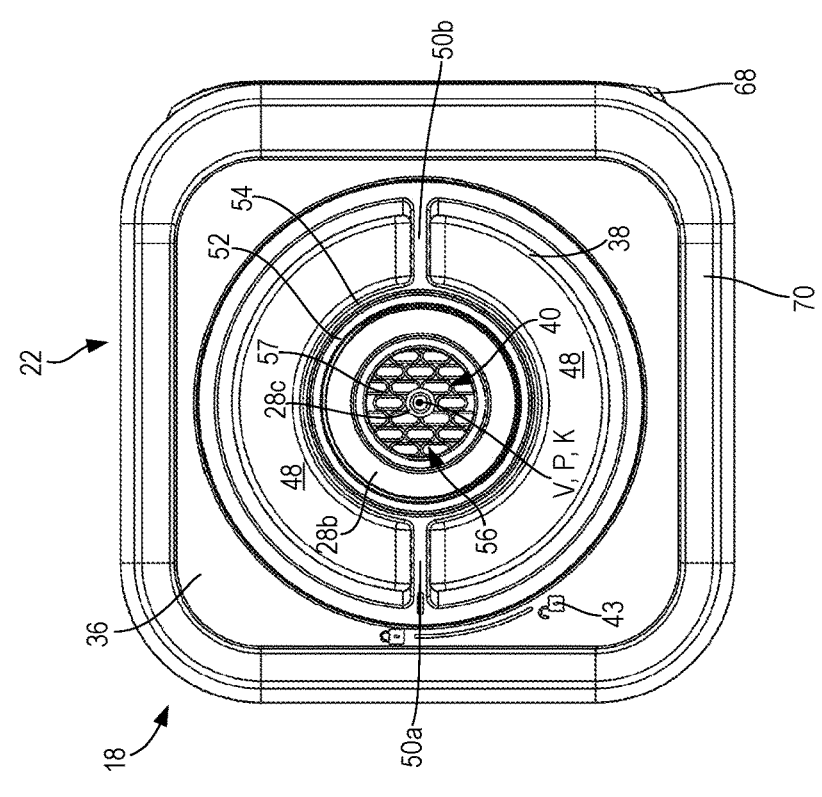

In FIG. 3 there is depicted a plan view of the end face 18 with the removable housing lid 22, i.e. with the direction of view along the coaxial axes latching axis V, prism axis P, and cartridge inlet axis K.

Figure 4:
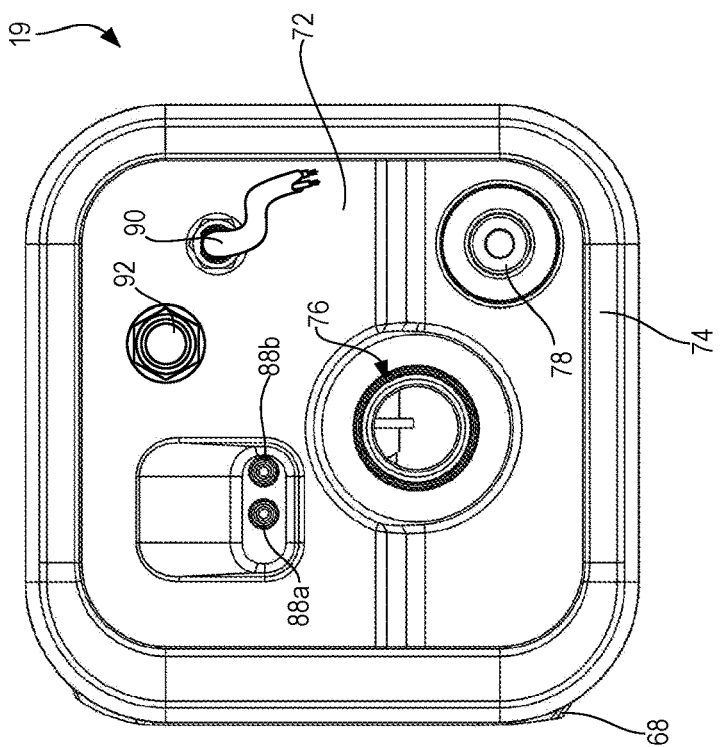

FIG. 4 shows a plan view of the end face 19 with housing-tight housing lid 72. The direction of view of FIG. 4 is opposite to that of FIG. 3.

Beyond the features already elucidated in connection with FIGS. 1 and 2, FIG. 4 shows connection nozzles 88a and 88b to which pressure acquisition hoses are connectable which at their other end lying distally from the connection nozzle 88a or 88b respectively are each connected with an inner region of a differential pressure flow sensor for measuring a proximal inspiratory and preferably also expiratory respiratory gas flow. The two inner regions are separated from one another in a manner known per se through a flow resistance, where the flow resistance is variable through the respiratory gas flow.

Given spatial availability of a power connection, the emergency ventilator 10 can be operated with energy from a public power supply grid via a power input 90. All electric functional units of the emergency ventilator 10 can then be supplied with grid voltage, normally with interposition of a power adaptor in the housing 12 which transforms to low voltage. The storage battery 32 can likewise be recharged. A socket 92 in the housing 12 is arranged for connecting an external sensor, in particular $CO_2$ sensor. Such a $CO_2$ sensor can for example be provided at a flow sensor coupled with the emergency ventilation device 10 and be coupled to a sensor arrangement.

Figure 5:
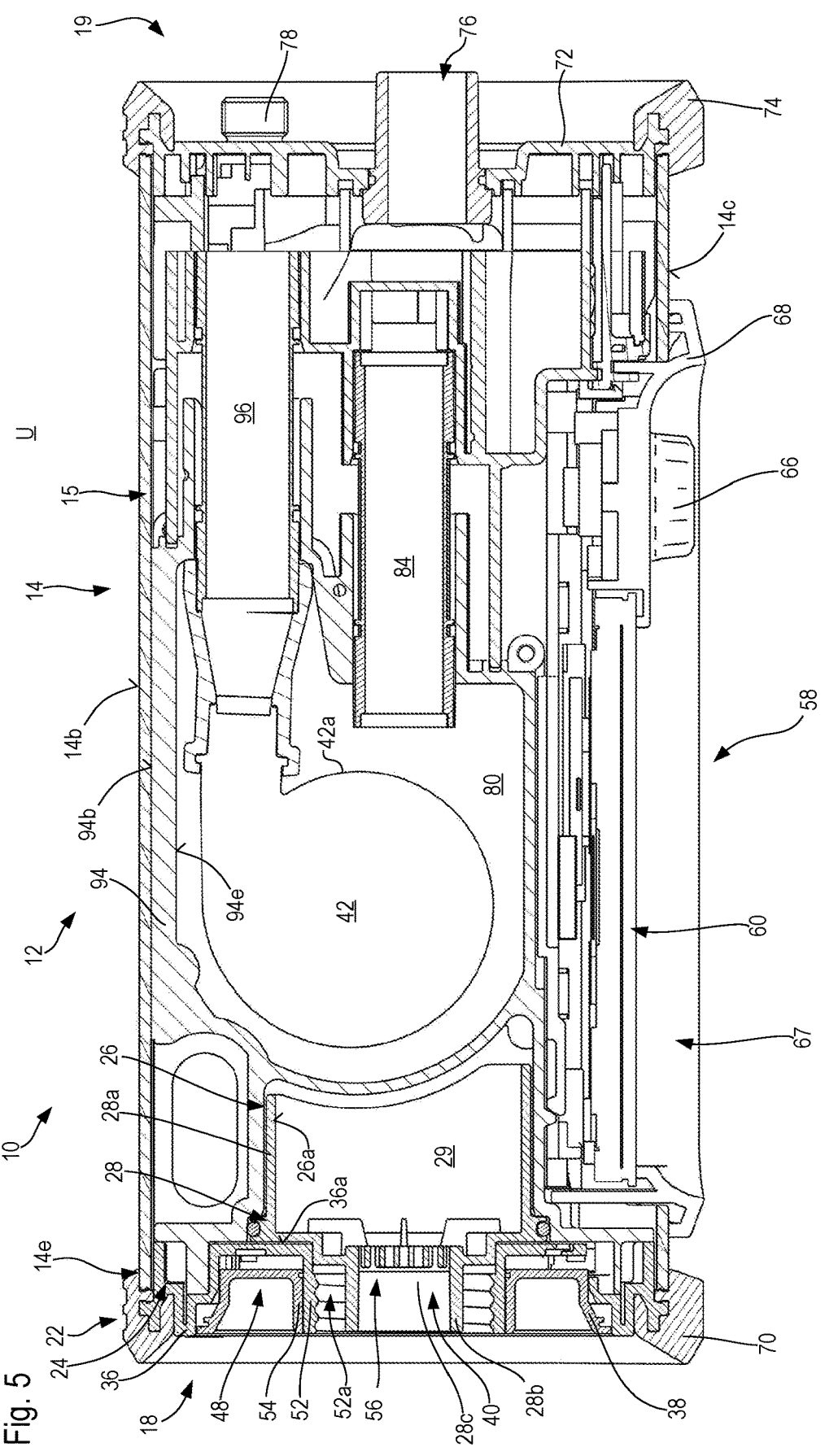
Figure 6:
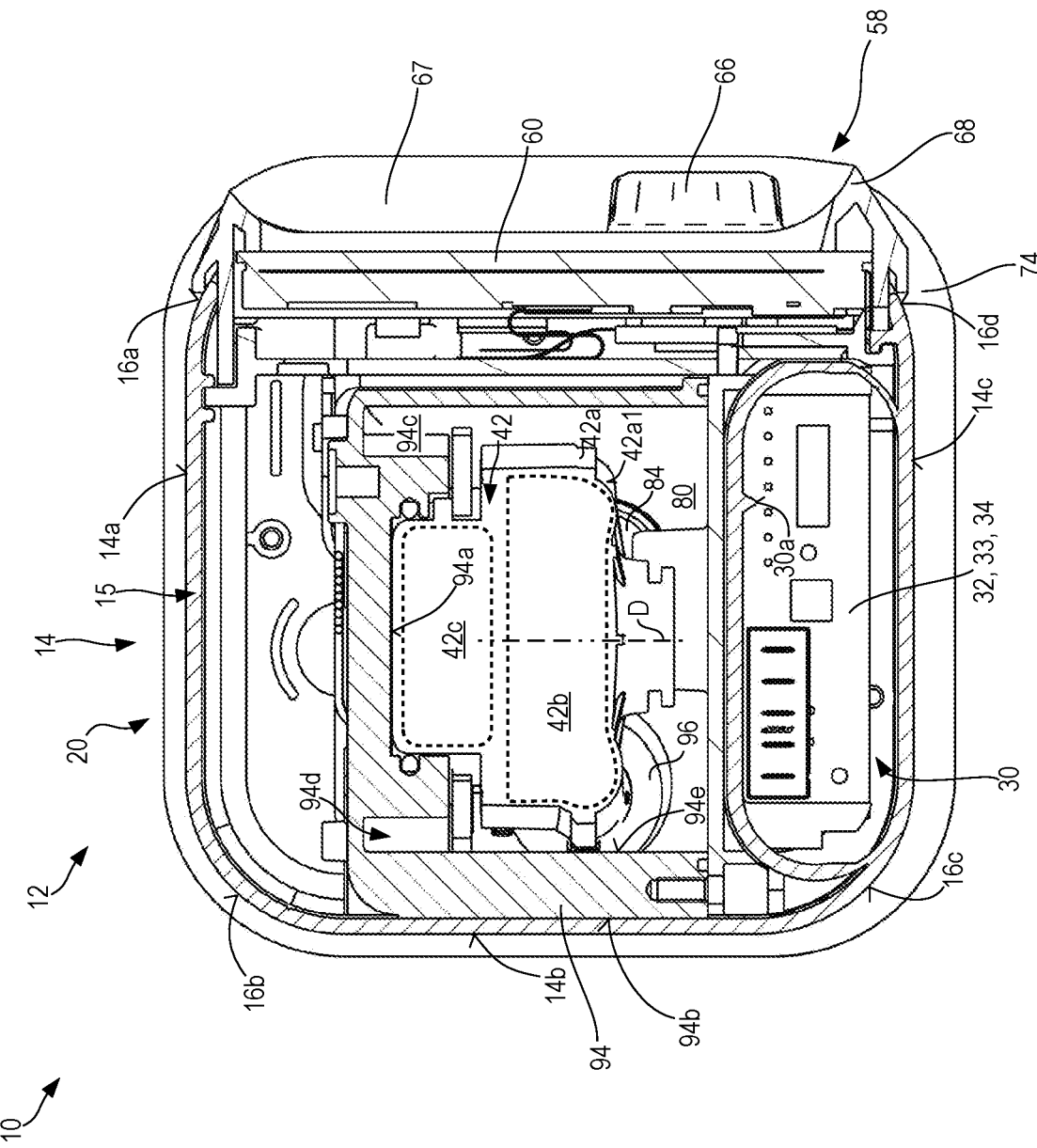
Figure 7:
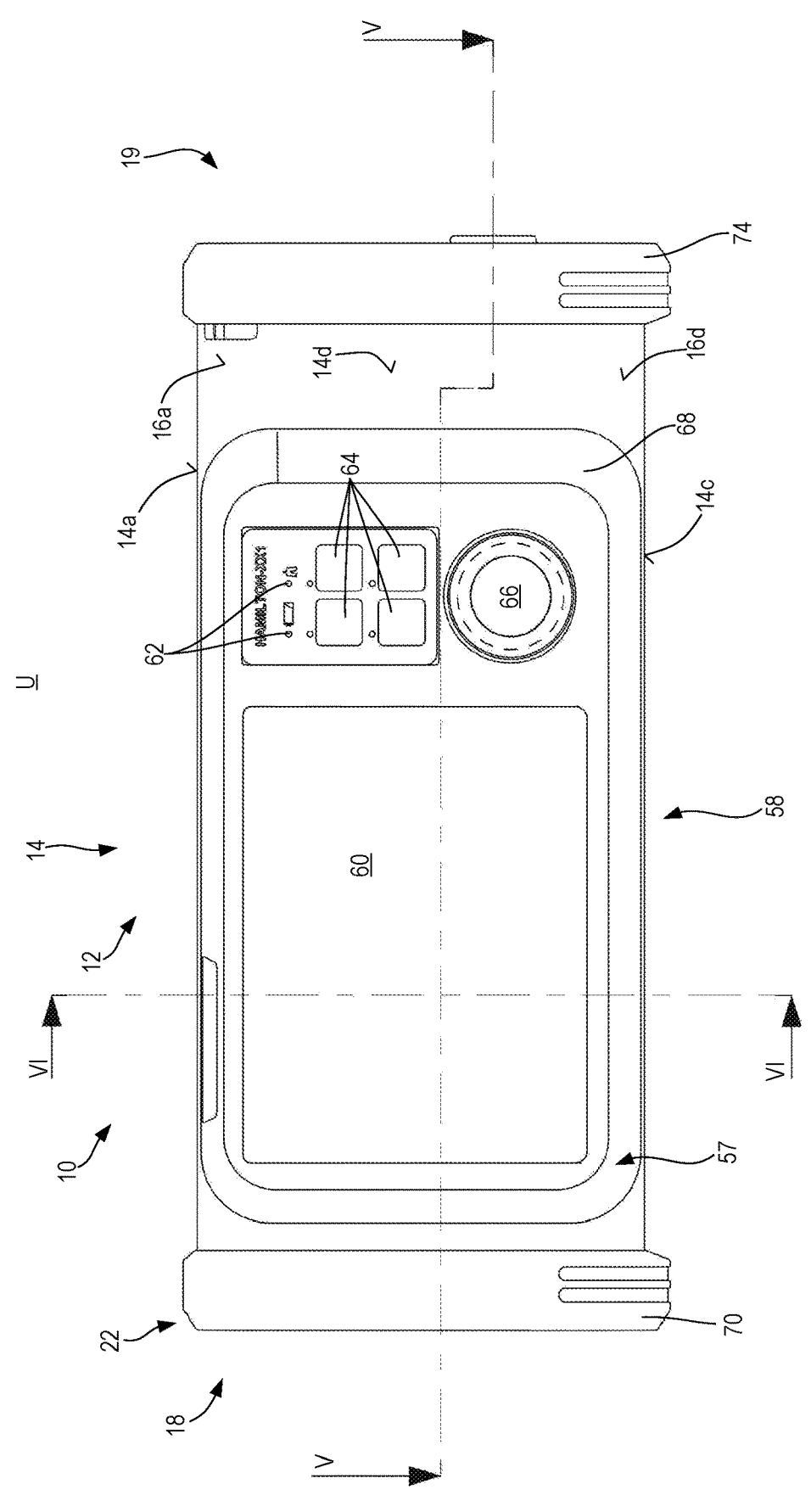

In the sectional views of FIGS. 2, 5, and 6, there is depicted in sectional view a heat-conducting body 94 to which the fan 42 is fastened.

As can be discerned in FIG. 6, in a lower section of the fan housing 42a there is accommodated an air conveyor 42b rotatably about a rotational axis D which is orthogonal to the planar area segment 14c and parallel to the drawing plane of FIGS. 2 and 6. An electric drive 42c located above the air conveyor 42b drives the air conveyor 42b which by way of example is configured as an impeller wheel to rotate. The lower section of the fan housing 42a can be configured as a separate conveyor housing part, on cost grounds for instance from a synthetic. To facilitate assembly, the conveyor housing part can itself in turn be configured in several parts.

A part of the fan housing 42a surrounding the drive 42c is attached in a recess at the heat-conducting body 94 bordered by a fan joint-face 94a with a small gap dimension of less than 1 mm, preferably of less than 0.3 mm, especially preferably gap-free, for example through gluing or soldering or welding or through fasteners such as bolts. This part of the fan housing 42a can be configured as a separate drive housing component, for better heat conduction for instance from an aluminum or metal alloy.

The fan housing 42a, preferably fabricated from aluminum by die casting or through machining from the solid, transfers heat from the fan 42 to the heat-conducting body 94. Since during the operation of the emergency ventilator 10 the drive 42c represents the most significant heat source inside the fan 42, the fan joint-face 94a preferably surrounds the region of the fan housing 42a which houses the drive 42c.

The heat-conducting body 94, likewise preferably fabricated from aluminum, exhibits at a distance from the fan joint-face 94a a housing joint-face 94b, with which the heat-conducting body 94 is connected with the housing 12 by full-face abutment against the inside of the housing section which exhibits the planar area segment 14b. The heat-conducting body 94 is preferably attached from outside with non-depicted bolts through clearance holes in the relevant housing section. The bolts penetrate through the clearance holes and are screwed into internal threads at the heat-conducting body 94. In this way the housing joint-face 94b can be full-face connected gap-free with the housing section.

Alternatively to the depiction in FIGS. 2 and 6, there can be arranged between the fan joint-face 94a and the fan housing 42a and/or between the housing joint-face 94b and the housing 12 intermediate layers which enhance heat conduction, for example as a paste-like layer of a heat-conductive paste or on the other hand preferably as a solid layer in the shape of a heat-conductive mat.

Heat transferred by the fan 42 to the heat-conducting body 94 follows the temperature gradient which during operation develops at the planar area segment 14b, where normally at the contact surface to the external environment U there is present the lowest temperature in the path from the fan 42 via the heat-conducting body 94 up to the housing 12. At the area segment 14b, the heat from the heat-conducting body 94 transferred by the fan 42 to the housing 12 is given off to the external environment U through convection and radiation. A convective flow can naturally develop due to the temperature difference between the area segment 14b and the external environment U and will be the more pronounced, the greater the temperature difference between the area segment 14b and the external temperature U. Since the tubular housing component 15 exhibiting the lateral surface 14 is preferably made from the good heat-conducting material aluminum, the housing component 15 conducts heat from the area segment 14b also to neighboring area segments 14a, 16b, 16c, 14c, etc, such that such area segments can also contribute to the dissipation of heat to the external environment U which are not directly in touching contact with the heat-conducting body 94.

The housing joint-face 94b is more than twice as large as the fan joint-face 94a.

As can be discerned in FIG. 6, a large part of the outer surface 42a1 of the fan housing 42a protrudes into the mixing chamber 80, where the protruding part of the outer surface 42a1 can be bathed by respiratory gas in the mixing chamber 80. Thus the respiratory gas conveyed by the fan 42 too, can contribute to the convective cooling of the fan 42 and of the emergency ventilator 10 overall. The outer surface 42a1 completely surrounds the rotational axis D of the air conveyor 42b in the circumferential direction.

The cooling effect of the respiratory gas and of the heat-conducting body 94 is preferably so good that the emergency ventilator 10 does not exhibit a dedicated cooling fan, such that preferably the fan 42 is the only fan in the emergency ventilator 10 for conveying respiratory gas.

In FIG. 5 there is discernible a respiratory gas duct 96 as output duct of the fan 42. On the pressure side of the fan 42, the fan 42 conveys respiratory gas through the respiratory gas duct 96 in the direction towards the respiratory gas output aperture 76. The respiratory gas duct 96 proceeds in the depicted embodiment example in a space-saving manner in parallel to the special gas supply line 84.

In the heat-conducting body 94 there can be configured channels 94c and 94d which increase the surface of the heat-conducting body 94, which, driven by the fan 42, at least section-wise can have flowing through them respiratory gas in the mixing chamber 80 and thus additionally transport heat convectively away from the heat-conducting body 94. This additionally increases the cooling effect of the respiratory gas and of the heat-conducting body 94.

A surface 94e of the heat-conducting body borders the mixing chamber 80 and can be bathed by respiratory gas.

As can be discerned in an overall view foremost of FIGS. 5 and 6, the integral heat-conducting body 94 surrounds the mixing chamber 80 on five sides. In the mixing chamber 80 there are arranged the air conveyor 42b and the part of the fan housing 42a which surrounds the air conveyor 42b. The part of the fan 42 protruding into the mixing chamber 80 is arranged on all sides at a distance from the heat-conducting body 94, in order to achieve the largest possible area which can give off heat to the respiratory gas in the mixing chamber 80.

Figure 8:
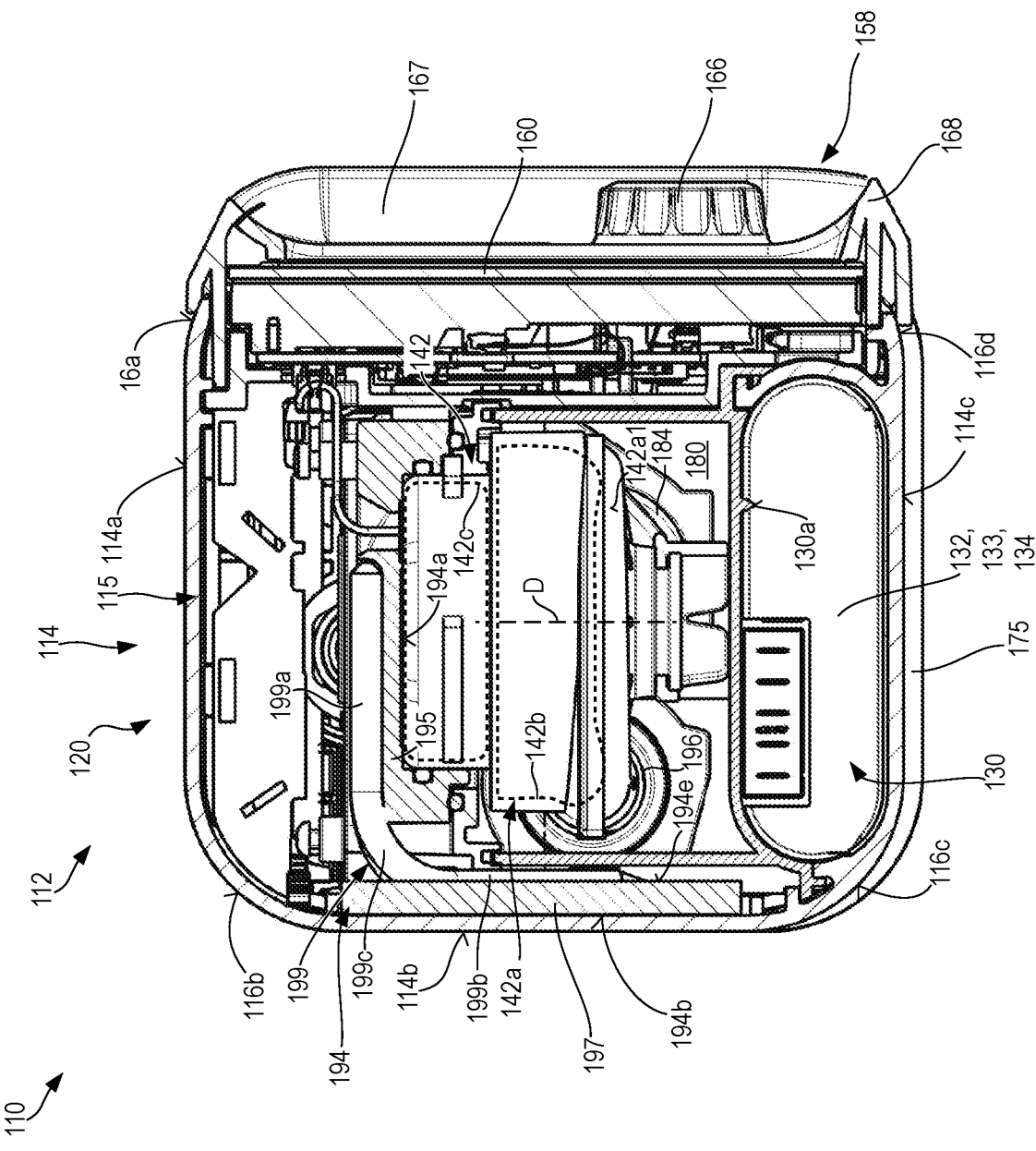

In FIG. 8 there is depicted in a cross-sectional view a second embodiment of an emergency ventilator 110 according to the invention. Identical and functionally identical components as in the first embodiment have the same reference numbers in the second embodiment, but increased numerically by 100.

The second embodiment shall be described hereunder only in so far as it differs from the first embodiment, to whose description otherwise reference shall also be made for elucidating the second embodiment.

A less significant detail of a difference between the first and the second embodiment lies in the no longer encircling elastomer ring at the longitudinal end of the housing 112 of the ventilator 110. Instead, there is provided at the housing 112 at the longitudinal end located behind the sectional plane only an elastomer foot 175. The foregoing notwithstanding, the second embodiment of the ventilator 110 can of course also exhibit at one or at both longitudinal ends an encircling elastomer ring as in the first embodiment.

An essential difference lies in the heat-conducting body 194 being configured in several parts. It exhibits a fan housing-side body component 195 and a housing-side body component 197 configured separately from the fan housing-side body component. The fan housing-side body component 195 exhibits, like the integral heat-conducting body 94 of the first embodiment, the fan joint-face 194a. The housing-side body component 197 exhibits, the same as the integral heat-conducting body 94 of the first embodiment, the housing joint-face 194b.

The two body components 195 and 197 of the heat-conducting body 194 are connected with one another in a heat-transferring manner through at least one heat pipe 199, in the present example through four heat pipes arranged one behind the other. The heat pipe 199 located nearest to the observer conceals here the heat pipes located behind it.

The similarly designed heat pipes 199 exhibit a heat-absorption zone 199a, which is formed by a straight end-side section of the heat pipe 199. To provide the best possible heat transfer from the fan housing-side body component 195 to the heat-absorption zone 199a, the heat-absorption zone 199a is connected with the former through a soldered connection.

At the end section opposite to the heat-absorption zone 199a, the heat pipes 199 exhibit a likewise straight section which forms a heat-emission zone 199b of the heat pipe 199. To provide the best possible heat transfer, the heat-emission zone 199b is likewise connected through a soldered connection with the housing-side body component 197 of the heat-conducting body 194.

In all other respects, the statements above regarding the first embodiment apply: heat is transferred from the fan 142 via the fan housing 142a through the fan joint-face 194a into the fan housing-side body component 195. The fan housing-side body component 195 conducts the heat transferred to it to the heat-absorption zone 199a of the heat pipe 199, which conducts the heat via a curved zone 199c located between the heat-absorption zone 199a and the heat-emission zone 199b to the heat-emission zone 199b. The heat-emission zone 199b gives off the heat to the housing-side body component 197, which in turn gives off the heat to the environment via the housing 112 and in particular via its surface region 114b lying nearest to the housing-side body component 197.

The heat-absorption zone 199a and the heat-emission zone 199b enclose in the depicted example an angle of 90°. The curved zone 199c is therefore preferably a quarter-torus.

In contrast to the first embodiment, the inward-facing surface 194e of the housing-side body component 197 is no longer in direct contact with the respiratory gas, but rather is shielded from the latter by an inner wall of the housing 112. This too, is merely a structural variation. The depiction in FIG. 8 notwithstanding, the internal surface 194e of the housing-side body component 197 can also border the mixing chamber 180 and be bathed by the respiratory gas. Nevertheless, it is preferable if the respiratory gas does not flow directly past the normally heated heat-emission zone 199b and take up heat from the latter.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. An emergency ventilator for emergency medicine artificial respiration of patients, comprising:
   a housing with an ambient air aspiration aperture and a respiratory gas output aperture, and
   a fan which is configured and arranged in the housing in order to convey ambient air from the ambient air aspiration aperture to the respiratory gas output aperture,
   where the fan comprises a fan housing with an air conveyor movable relative to the fan housing and where the fan housing is arranged housing-tight in the housing; where the fan housing is fixed to the housing with the interposition of a heat-conducting body, where the heat-conducting body comprises a material or is made from a material which is chosen out of light metal, non-ferrous metal, and/or a synthetic filled with heat-conducting filling material,
   wherein an outer surface of the fan housing is exposed in a section of a flow path from the ambient air aspiration aperture to the respiratory gas output aperture in such a way that during a ventilation operation of the emergency ventilator it can be bathed by respiratory gas conveyed by the fan and wherein a section of the fan housing which houses a drive is connected with the heat-conducting body and a section of the fan housing which exhibits the air conveyor protrudes into the flow path of the respiratory gas from the ambient air aspiration aperture to the respiratory gas output aperture.

2. The emergency ventilator according to claim 1, wherein the fan housing is connected rigidly with the heat-conducting body.

3. The emergency ventilator according to claim 1, wherein the heat-conducting body is connected rigidly with the housing.

4. The emergency ventilator according to claim 1, wherein the heat-conducting body exhibits at least one duct routed in the heat-conducting body which forms at least one part of a flow path from the ambient air aspiration aperture to the respiratory gas output aperture in such a way that during the ventilation operation of the emergency ventilator flow through the at least one duct of respiratory gas conveyed by the fan is possible.

5. The emergency ventilator according to claim 1, wherein a surface of the heat-conducting body forms a wall of a region enclosing a respiratory gas.

6. The emergency ventilator according to claim 5, wherein an outer surface of the fan housing is exposed in a section of a flow path from the ambient air aspiration aperture to the respiratory gas output aperture in such a way that during the ventilation operation of the emergency ventilator it can be bathed by respiratory gas conveyed by the fan; the heat-conducting body surrounding a section of the flow path of the respiratory gas on at least three sides forming a recess where the outer surface of the fan housing which can be bathed by respiratory gas is arranged in the recess formed by the heat-conducting body.

7. The emergency ventilator according to claim 5, wherein an outer surface of the fan housing is exposed in a section of a flow path from the ambient air aspiration aperture to the respiratory gas output aperture in such a way that during the ventilation operation of the emergency ventilator it can be bathed by respiratory gas conveyed by the fan; the heat-conducting body surrounding a mixing chamber on four sides forming a recess where the outer surface of the fan housing which can be bathed by respiratory gas is arranged in the recess formed by the heat-conducting body.

8. The emergency ventilator according to claim 1, wherein the air conveyor is an air conveyor rotationally movable relative to the fan housing, where at least the outer surface of the fan housing which can be bathed by respiratory gas is an outer surface surrounding a rotational axis of the air conveyor.

9. The emergency ventilator according to claim 1, wherein the air conveyor is an air conveyor rotationally movable relative to the fan housing, where at least the outer surface of the fan housing which can be bathed by respiratory gas is an outer surface surrounding a rotational axis of the air conveyor and surrounding completely along a closed path.

10. The emergency ventilator according to claim 1, wherein the fan housing comprises a material or is made from a material which is chosen out of light metal, non-ferrous metal, and/or a synthetic filled with heat-conducting filling material.

11. The emergency ventilator according to claim 1, wherein the housing comprises a material or is made from a material which is chosen out of light metal, non-ferrous metal, and/or a synthetic filled with heat-conducting filling material.

12. The emergency ventilator according to claim 1, wherein the light metal comprises aluminum, magnesium, an aluminum alloy, and/or a magnesium alloy; the non-ferrous metal comprises copper and/or a copper alloy; and the heat-conducting filling material comprises a metal, and/or a ceramic, and/or graphite, and/or carbon.

13. The emergency ventilator according to claim 12, wherein the heat-conducting body comprises the material or is made from the material which is the synthetic filled material with the heat-conducting filling material and the heat-conducting filling material comprises carbon nanotubes with a heat conductance of at least 14 W/(mK).

14. The emergency ventilator according to claim 1, wherein the heat-conducting body exhibits a fan joint-face which lies opposite a section of the fan housing and exhibits a housing joint-face which faces towards an inner surface of the housing, where the housing joint-face is at least twice as large as the fan joint-face.

15. The emergency ventilator according to claim 14, wherein the housing joint-face is at least six times as large as the fan joint-face.

16. The emergency ventilator according to claim 14, wherein the housing joint-face is planar.

17. The emergency ventilator according to claim 1, wherein the emergency ventilator exhibits a control device which is configured to operate the fan only during inspiratory phases.

18. An emergency ventilator for emergency medicine artificial respiration of patients, comprising:
    a housing with an ambient air aspiration aperture and a respiratory gas output aperture, and
    a fan which is configured and arranged in the housing in order to convey ambient air from the ambient air aspiration aperture to the respiratory gas output aperture,
where the fan comprises a fan housing with an air conveyor movable relative to the fan housing and where the fan housing is arranged housing-tight in the housing; where the fan housing is fixed to the housing with the interposition of a heat-conducting body, where the heat-conducting body comprises a material or is made from a material which is chosen out of light metal, non-ferrous metal, and/or a synthetic filled with heat-conducting filling material,
wherein a surface of the heat-conducting body forms a wall of a region enclosing a respiratory gas and
wherein an outer surface of the fan housing is exposed in a section of a flow path from the ambient air aspiration aperture to the respiratory gas output aperture in such a way that during a ventilation operation of the emergency ventilator it can be bathed by respiratory gas conveyed by the fan; the heat-conducting body surrounding a mixing chamber on four sides forming a recess where the outer surface of the fan housing which can be bathed by respiratory gas is arranged in the recess formed by the heat-conducting body.

19. An emergency ventilator for emergency medicine artificial respiration of patients, comprising:
    a housing with an ambient air aspiration aperture and a respiratory gas output aperture, and
    a fan which is configured and arranged in the housing in order to convey ambient air from the ambient air aspiration aperture to the respiratory gas output aperture,
where the fan comprises a fan housing with an air conveyor movable relative to the fan housing and where the fan housing is arranged housing-tight in the housing; where the fan housing is fixed to the housing with the interposition of a heat-conducting body, where the heat-conducting body comprises a material or is made from a material which is chosen out of light metal, non-ferrous metal, and/or a synthetic filled with heat-conducting filling material, wherein the heat-conducting body exhibits a fan joint-face which lies opposite a section of the fan housing and exhibits a housing joint-face which faces towards an inner surface of the housing, where the housing joint-face is at least twice as large as the fan joint-face and wherein the housing joint-face is at least six times as large as the fan joint-face.

20. The emergency ventilator according to claim 19, wherein an outer surface of the fan housing is exposed in a section of a flow path from the ambient air aspiration aperture to the respiratory gas output aperture in such a way that during a ventilation operation of the emergency ventilator it can be bathed by respiratory gas conveyed by the fan.

21. The emergency ventilator according to claim 20, wherein a section of the fan housing which houses a drive is connected with the heat-conducting body and a section of the fan housing which exhibits the air conveyor protrudes into the flow path of the respiratory gas from the ambient air aspiration aperture to the respiratory gas output aperture.

* * * * *